United States Patent [19]

Nagase

[11] Patent Number: 4,618,934
[45] Date of Patent: Oct. 21, 1986

[54] ULTRASONIC MICROSCOPE APPARATUS

[75] Inventor: Masashi Nagase, Yokohama, Japan

[73] Assignee: Tokyo Shibaura Denki Kabushiki Kaisha, Kawasaki, Japan

[21] Appl. No.: 565,479

[22] Filed: Dec. 27, 1983

[30] Foreign Application Priority Data

Dec. 28, 1982 [JP] Japan .................................. 57-233412

[51] Int. Cl.⁴ ...................... G06F 15/20; G01N 29/04
[52] U.S. Cl. .................................. 364/507; 364/490; 73/620
[58] Field of Search ............................. 364/488–490, 364/507, 551, 571; 73/606, 607, 620

[56] References Cited

U.S. PATENT DOCUMENTS

| | | | |
|---|---|---|---|
| 3,857,052 | 12/1974 | Beller | 73/620 |
| 3,996,792 | 12/1976 | Kubota et al. | 364/507 |
| 4,052,889 | 10/1977 | Mucciardi et al. | 73/620 |
| 4,240,295 | 12/1980 | Uranishi | 73/607 |
| 4,292,848 | 10/1981 | Rainey et al. | 73/620 |
| 4,312,229 | 1/1982 | Hurwitz et al. | 73/620 |
| 4,484,820 | 11/1984 | Rosencwaig | 73/606 |
| 4,491,020 | 1/1985 | Chubachi | 73/606 |

OTHER PUBLICATIONS

"Acoustic Microscopy–Non-Destructive Analysis of Internal Microstructure", vol. 19, No. 6, Jun. 1979, Published in Circuit Manufacturing.

"High Resolution Ultrasonic System for the Real-Time Video Imaging of Internal Flaw" by Glenn et al, Published in Materials Evaluation, Jan. 1982.

Quate et al., "Acoustic Microscopy with Mechanical Scanning–A Review," Proceedings of the IEEE, vol. 67, No. 8, Aug. 1979.

Hollis et al., "Defect Detection for Microelectronics by Acoustic Microscopy," Scanned Image Microscopy (Academic Press), 1980.

Primary Examiner—Gary Chin
Attorney, Agent, or Firm—Finnegan, Henderson, Farabow, Garrett & Dunner

[57] ABSTRACT

An integrated circuit is operated under predetermined conditions. The operating integrated circuit is scanned by an ultrasonic beam. Ultrasonic images obtained by the scanning operation are stored into memories, mutually computed, and finally displayed by a color display.

9 Claims, 4 Drawing Figures

ULTRASONIC MICROSCOPE APPARATUS

BACKGROUND OF THE INVENTION

The present invention relates to an ultrasonic microscope apparatus for observing the internal structure of an object being measured by ultrasonic waves.

Integrated circuits (ICs), for example, are manufactured through many process steps. In the course of manufacturing ICs, IC chips sometimes sustain defects. If a defect is located in an important region of the IC chip, the electrical performance of the IC is seriously degraded. Most of the defects appear in the boundary layers in the area of the chip surface. Such defects cannot be inspected by an optical microscope. To cope with this problem, an ultrasonic microscope apparatus has been proposed as an effective means for inspecting defects and determining the resiliency of the material in the surface region of the object under measurement.

To form an image with an ultrasonic microscope apparatus, ultrasonic waves are irradiated from a sound source and converged, by an acoustic lens, onto a microspot. The microspot is used to achieve a two-dimensional scanning of the surface of the object. The ultrasonic waves reflected and scattered by the object under measurement are collected and converted into electrical signals. In synchronism with the scanning of the ultrasonic microspot, the electrical signals are two-dimensionally visualized on a CRT, for example, in the form of an ultrasonic image.

FIG. 1 illustrates, in block form, a conventional ultrasonic microscope apparatus. High frequency pulses generated by a pulse generator 1 are applied, through a buffer amplifier 2 and a circulator 3, to a piezoelectric transducer 5 provided near the rear end of an acoustic lens 4. The piezoelectric transducer 5 made of zinc oxide (ZnO), for example, generates an ultrasonic wave of a frequency corresponding to that of the high frequency pulse voltage and an amplitude proportional to the pulse voltage amplitude. The ultrasonic wave is converged by the acoustic lens 4, which may be, for example, a saffire rod of a plano-convex shape. As shown, the acoustic lens 4 is so arranged that its plano side is positioned near the piezoelectric transducer 5, and its convex side is polished and shaped in such a manner as to have a spherical surface. The acoustic lens 4 converges ultrasonic waves onto a microspot on an object under measurement 6, such as an IC chip. The space between the spherical surface of the acoustic lens 4 and the object 6 is filled with a medium 7 such as liquid or gas. When gas is used as the medium 7; as its pressure is increased, the resolution of the ultrasonic image is improved. The ultrasonic wave is reflected or scattered from the object depending on the acoustical characteristics of the surface or surface region of the object. Reflected or scattered ultrasonic waves are collected by the acoustic lens 4. The collected ultrasonic wave energy is converted, by the piezoelectric transducer 5, into an electrical signal; and is applied to a gate 8, through the circulator 3. The gate 8 selects the necessary information signals and applies them to a mixing circuit 11, through an attenuator 9 and a high frequency amplifier 10. In the mixing circuit 11, the selected signal is mixed with a signal output from a local oscillator 12, and is converted into an intermediate frequency signal. The intermediate frequency signal is amplified by an intermediate frequency amplifier 13. The output signal of the intermediate frequency amplifier 13 is detected by a detector 14, and is then applied to a scanning converter 18, via a blanking circuit 15, a peak detector 16 and a limiter circuit 17.

A control unit 19 drives, through a scanning drive circuit 20, a stage 21 with the object 6 placed thereon, allowing the object under measurement 6 to be scanned by the ultrasonic spot. For Y-direction scanning of the object 6, the stage 21 is driven at a low rate of speed, using a lead screw (not shown). For X-direction scanning, the acoustic lens 4 is driven at a high speed using a voice coil actuator. The Y and X-direction scanning movements are concurrently performed to produce two dimensional scanning. In synchronism with this scanning, the control unit 19 applies a signal to the gate 8, the blanking circuit 15 and the scanning converter 18, to produce brightness signals at individual positions in the vicinity of the surface of the object 6. The brightness signals are applied to a monitor 22; which, in turn, visualizes them as an image of the object 6, in synchronization with the two-dimensional scanning operation.

The ultrasonic microscope apparatus thus constructed, when employed in inspecting defects in and on integrated circuits, for example, can inspect defective portions of the integrated circuits, which portions cannot be found by observation of only the surfaces of the IC chips. Thus, the ultrasonic microscope apparatus can accurately inspect defective portions in the semiconductor structure. The ultrasonic microscope apparatus is thus very useful when applied to the testing of high density integrated circuits of the multilayered structure type, which circuits have gradually come into use in recent years.

The aluminum interconnection wires of IC chips may have protruding portions. Thermal stresses generated under operating conditions cause those protruding portions to contact with other wires or parts. To determine the cause of the defect, it is necessary to recreate the same conditions which caused the defect. Toward this end, the electrical operating conditions and ambient conditions, e.g., temperature and humidity, are changed every measurement to observe the internal structure of the IC chip. The ultrasonic microscope apparatus of FIG. 1 requires a manual operation for setting and changing the operating and ambient conditions.

Further, the results of measurement must be photographed, for the purpose of recording them. The actual photograph is, of course, troublesome for an operator, accompanied by complicated and highly skilled operations. Careful comparison of the photographs taken is essential for proper defect inspection. This comparative, visual check is based on the judgment faculties of the operator. Therefore, to obtain an accurate and reliable check, the inspectors must be highly skilled. Otherwise, the results of the inspection may frequently be unreliable; as well as impracticable, in terms of the time consumed.

SUMMARY OF THE INVENTION

Accordingly, a primary object of the present invention is to provide an ultrasonic microscope apparatus in which various operating conditions may be readily imposed on the integrated circuits under measurement, and the comparison of the measured data on the integrated circuits may be done in a relatively easy manner.

According to the present invention, the ultrasonic microscope apparatus provided is one in which selected electrical operating and ambient conditions of the integrated circuits under measurement may be easily set, the measured data is stored at high speed; and the data is comparatively analyzed with the results displayed in a color picture.

According to the present invention there is provided an ultrasonic microscope apparatus comprising means for setting the electrical operating conditions of an integrated circuit, means for obtaining ultrasonic images by scanning the integrated circuit with an ultrasonic beam, means for individually storing the ultrasonic images, means for mutually computing the data on said ultrasonic images, which is stored in said memory means, and means for displaying the results of computation of said computing means and said ultrasonic images stored in said memory means.

DETAILED DESCRIPTION OF THE PREFERRED EMBODIMENT

Figure 1:
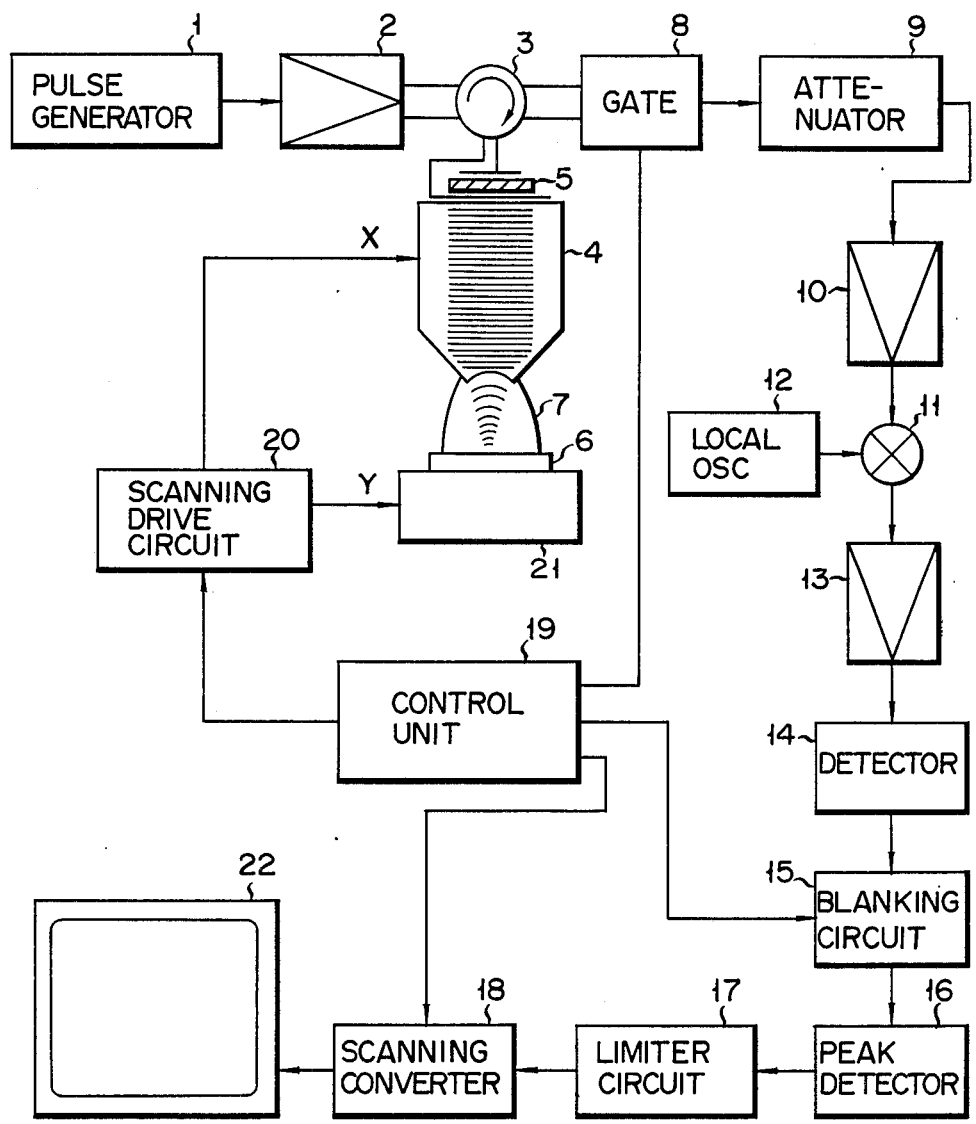
FIG. 1 is a block diagram of a conventional ultrasonic microscope apparatus.
Figure 2:
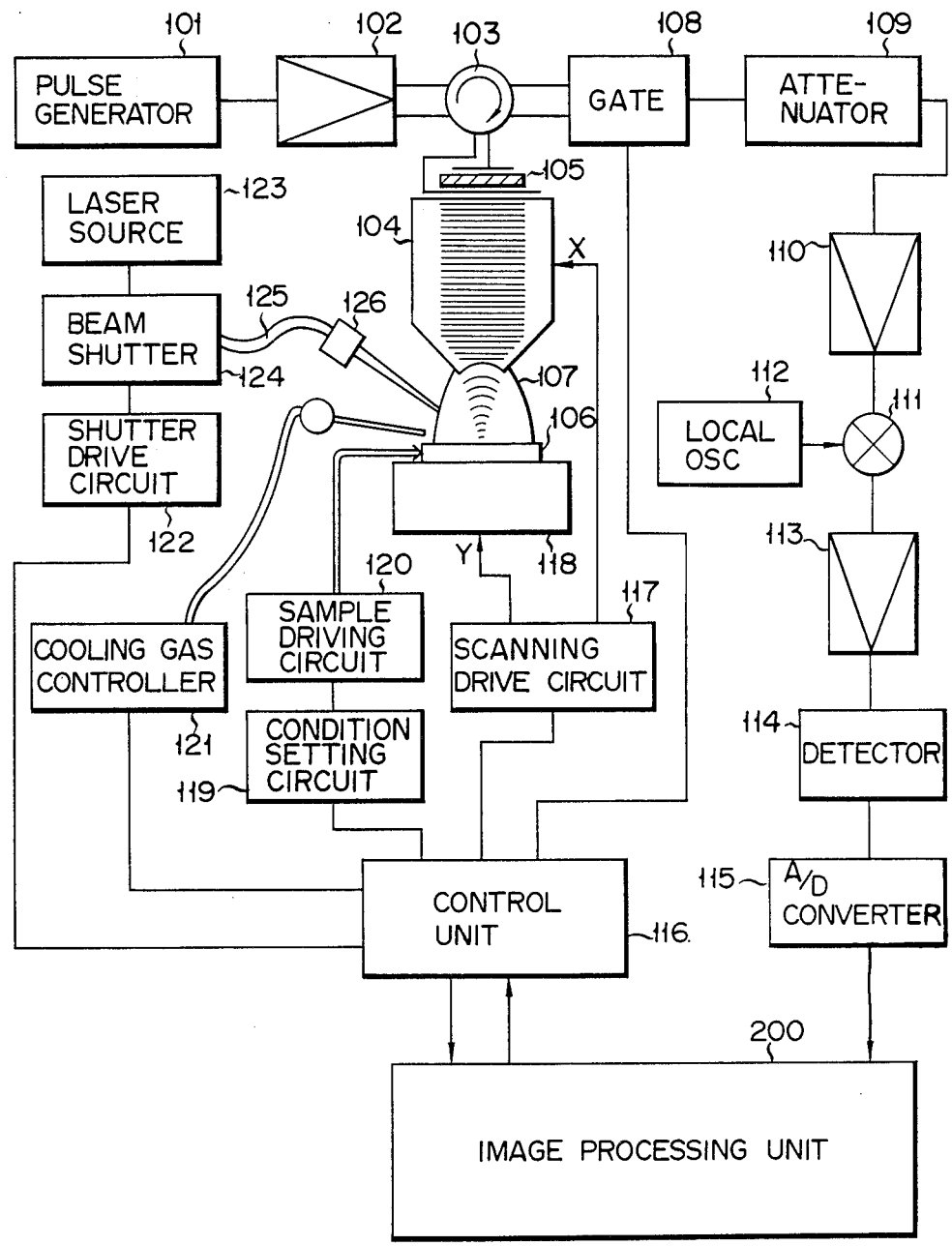
FIG. 2 is a block diagram of an ultrasonic microscope apparatus according to the present invention.

A preferred embodiment of an ultrasonic microscope apparatus according to the present invention may be described as follows, with reference to the accompanying drawings. FIG. 2 shows, in block form, an ultrasonic microscope apparatus for testing integrated circuits, which is an embodiment of the present invention. In FIG. 2, a high frequency pulse generator 101 generates high frequency pulses. Pulses of high frequency, e.g., 10 GHz generated by a pulse generator 101 are applied through a buffer amplifier 102 and a circulator 103 to a piezoelectric transducer 105 provided near the rear end of an acoustic lens 104. The piezoelectric transducer 105 generates an ultrasonic wave with the same frequency as that of the high frequency pulse generator. The ultrasonic wave is converged, by the acoustic lens 104, which may be a saffire rod of a plano-convex type. As shown, the acoustic lens 104 is so arranged that its plano side is positioned near the piezoelectric transducer 105, and its convex side is polished and shaped in such a manner as to have a spherical surface.

The acoustic lens 104 converges ultrasonic waves into a microspot on an object under measurement 106. The space between the spherical surface of the acoustic lens 104 and the object under measurement 106 is filled with a medium 107 such as a liquid or a gas. When a gas is used for the medium 107; as its pressure is increased, the resolution of the ultrasonic image is improved. The ultrasonic wave, then reaching the object under measurement 106, is reflected, scattered and transmitted, depending on the acoustical characteristics of the surface of the object or in that vicinity. Reflected or scattered ultrasonic wave energy from the object under measurement 106 is collected by the acoustic lens 104. The collected ultrasonic wave energy is converted by the piezoelectric transducer 105 into an electrical signal and is applied to a gate 108, through the circulator 103. The gate 108 selects only necessary information signals and applies them to a mixing circuit 111 through an attenuator 109 and a high frequency amplifier 110. In the mixing circuit 111, the selected signal is mixed with a signal outputted from a local oscillator 112, and is then converted into an intermediate frequency signal. The intermediate frequency signal is amplified by an intermediate frequency amplifier 113. The output signal of the intermediate frequency amplifier 113 is detected by a detector 114, and then is applied to an analog to digital (A/D) converter 115, where it is digitized. The output digital signal from the A/D converter 115 is applied to an image processing unit 120.

A control unit 116 drives, through a scanning drive circuit 117, a stage 118 supporting the object under measurement 106, allowing the object under measurement 106 to be scanned by the ultrasonic spot. For Y-direction scanning of the object, the stage 118 is driven at a low rate of speed, using a lead screw (not shown). For an X-direction scanning, the acoustic lens 104 is driven at a high rate of speed, using a voice coil actuator (not shown). Y and X-direction scanning is concurrently performed to realize two dimensional scanning. In synchronism with this scanning, the control unit 116 applies a signal to the gate 108 and the image processing unit 200, to generate brightness (reflected acoustic intensity) signals at individual positions in the vicinity of the surface of the object under measurement 106. The brightness signals of each image are stored in a digital memory, by means of the image processing unit 200. An appropriate comparative computation is performed on desired images, for example, by measuring the difference in intensity of corresponding pixels of the two images, and the results of the computation are then applied to a monitor; which, in turn, visualizes them as an image of the object under measurement 106.

For setting operating conditions on the object, a signal from the control unit 116 is applied to a condition setting circuit 119; and, then, to the integrated circuit of the object 106, via a sample driving circuit 120. This signal appropriately sets a power source voltage, a clock signal, and various types of input/output signals. For setting ambient conditions, for example, temperature, on the object 106, a signal from the control unit 116 is applied to a cooling gas controller 121, to control the flow of cooling gas. Further, the control unit 116 applies a signal to a shutter drive circuit 122, to thereby control a beam shutter 124, such as a Q switch, which is positioned in the optical path from a laser beam source 123. The beam from source 123 is chopped in such a way as to control the period and pulse width of the laser beam. Then, it is channelled via an optical fiber 125 to an optical lens system 126, where it is converged into a light spot of the required size. This light spot thermally irradiates the object 106. The optical lens system 126 is so mounted on the stage 118 that it can maintain a predetermined radiating position when the stage 118 is moved, in scanning the object with the ultrasonic beam.

The irradiation position setting effected by the laser beam may be made while observing the object with an optical microscope (not shown). When the laser output is so large that it is dangerous to directly observe the object, or make precise observations from the irradiating position, a laser device of a small output and at a frequency which is within a visible wave range, such as an He—Ne laser beam with an output of several watts, may additionally be used in such a manner that its optical path is set to coincide with that of the heating laser beam. When observing the irradiating position by the optical microscope, this smaller laser is set to irradiate the desired position, thus finding the correct irradiating position for the heating laser beam.

Figure 3:
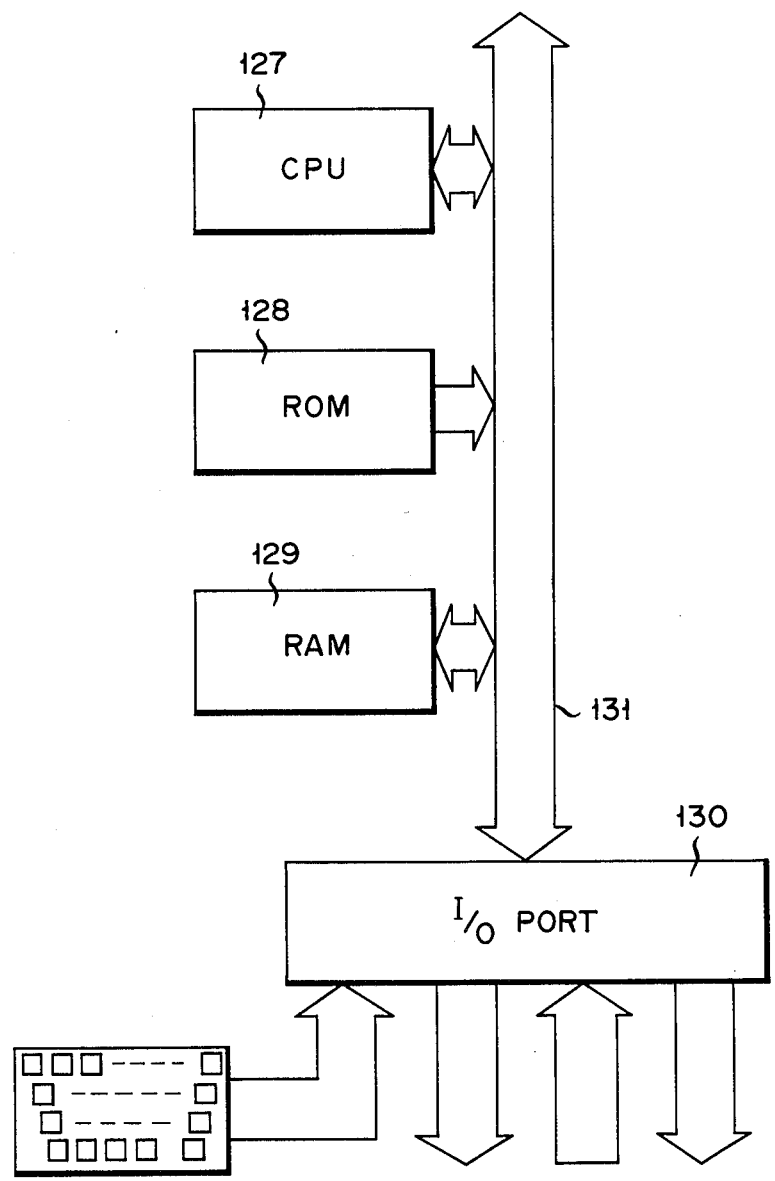
FIG. 3 is a block diagram of a control unit used in the FIG. 2 apparatus.

FIG. 3 shows the arrangement of circuits within the control unit 116 wherein a CPU 127, a ROM (read only memory) 128, a RAM (random access memory) 129, and an input/output port 130 are interconnected through a bus 131. The control unit 116 executes a program stored in the ROM 128; and controls, through an input/output port 130 the gate 108, scanning drive circuit 117, the condition setting circuit 119, the cooling gas controller 121, the shutter drive circuit 122 and the image processing unit 200.

Figure 4:
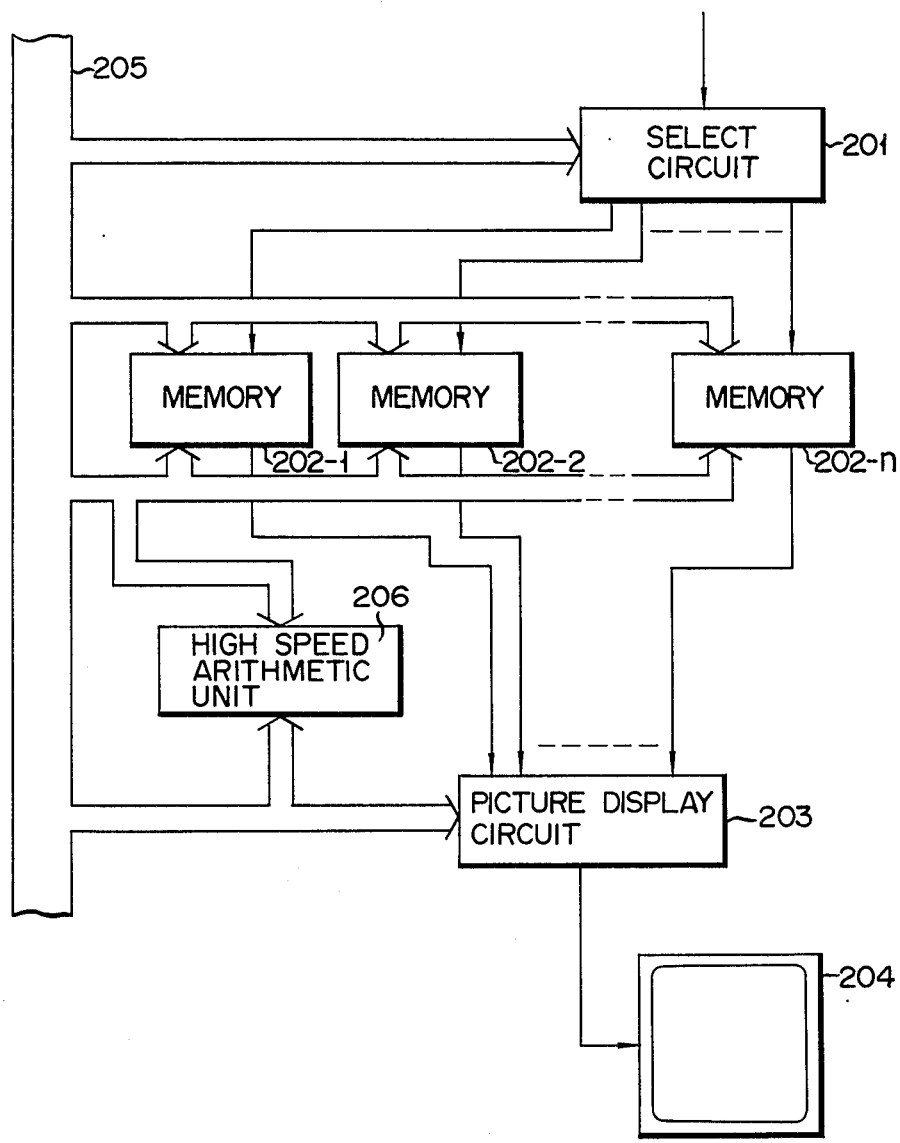
FIG. 4 is a block diagram of an image processing unit such as that which used in the FIG. 2 apparatus.

An example of the image processing unit 200 is illustrated in FIG. 4. The output representing an image of the object from the A/D converter 115 is applied to a select circuit 201. The select circuit 201 selects frames of the image and loads them, one at a time into their respective memories 202-1 to 202-n. A picture display circuit 203 reconstructs a single image, using the data from the memories 201-1 to 202-n, and color-displays it via a monitor 204. The contents of the memories 202-1 to 202-n are mutually computed and the results of the computation are loaded into proper memories 202 or are displayed in a color picture. Therefore, only different portions of two different images are displayed in distinctive colors, to clearly present those different portions. The data from the memories 202-1 to 202-n is applied, through a bus 205 in the control unit 116, to a high speed arithmetic unit 206, where that data may be processed at a high rate of speed.

The condition setting circuit 119 and the sample driving circuit 120 may be so modified as to operate in various modes, for use with the integrated circuit of the object under measurement 106.

Infrared rays, for example, may be used in place of the laser beam, in heating the object.

The laser source 123 may be of either a continuous or pulsative emitting type. In the case of the pulse laser, its output may be properly adjusted by controlling the period of the pulse laser beam by the control unit 116. The laser source 123 may be the solid, liquid or semiconductor laser. If the irradiating area of the laser beam is satisfactorily small, the object can be directly irradiated with the laser beam from the end of the optical fiber 125, without using the optical lens system 126. In locally heating the object 106 by the laser beam, it may be irradiated, not only from the obverse side thereof, but from the reverse side, as well. In the latter case, the infrared laser with a long wavelength is effective. For chopping the laser beam, the Q switch may be replaced by a rotating disc with a hole or cut-away portion on the periphery. An optical modulator with electrochemical effects, or a Pockels cell may be used for the same purposes; or, the same results may be obtained via the Kerr effect. The intensity of the laser beam may be controlled by on/off modulating an ultrasonic-light intensity modulator. Further, the Q switch may be replaced by an ultrasonic polarizer, a supersaturation dye laser, a rotating prism, etc.

To reproduce a defect causing state by locally heating the object 106, the IC chip is so driven that a desired portion thereof consumes substantial electrical power. Toward this end, the combination of the items of input data or the order of inputting these items may be changed. Alternatively, the power source voltage or input signal voltage may be changed, or the drive frequency may be changed.

If such an arrangement is employed, any operating and ambient conditions may be set by the control unit 116. As a result, the object under measurement 106 is entirely driven under the control of the control unit 116. Further, the conditions once set may be easily reproduced at any time. Furthermore, the measured data collected under a plurality of measuring conditions is stored in the memories. That data is read out and properly processed for display in a color picture. Therefore, testing of the object under measurement is facilitated. Changes in and differences between the items of measured data may be clearly displayed, without requiring special skills. A specific position in the integrated circuit element may be heated at will by the laser beam, to readily reproduce a defect causing state via thermal stress. This fact, along with the storage of a plurality of images in the memories 202-1 to 202-n, facilitates the inspection of defects within the IC chip.

What is claimed is:

1. An ultrasonic microscope apparatus comprising:
   means for varying the operating conditions of an integrated circuit;
   means for obtaining ultrasonic images of said integrated circuit by scanning said circuit with an ultrasonic beam;
   memory means for individually storing said ultrasonic images;
   means for calculating difference values for corresponding portions of said stored ultrasonic images produced for different operating conditions of said circuit; and
   means for displaying said difference values to provide information regarding defects in said circuit.

2. An ultrasonic microscope apparatus according to claim 1, further comprising means for heating said integrated circuit.

3. An ultrasonic microscope apparatus according to claim 2, in which said heating means is a laser.

4. An ultrasonic microscope apparatus according to claim 1, further comprising means for cooling said integrated circuit.

5. An ultrasonic microscope apparatus according to claim 4, in which said cooling means blows gas toward said integrated circuit.

6. An ultrasonic microscope apparatus according to claim 1, in which said ultrasonic image is converted into digital signals and stored in said memory means.

7. An ultrasonic microscope apparatus according to claim 1, in which the calculation of said difference values is executed by a high speed arithmetic unit.

8. An ultrasonic microscope apparatus according to claim 1, further comprising a control unit which controls said means for varying the operating conditions of said integrated circuit to provide changes in the electrical operating conditions of said circuit.

9. An ultrasonic microscope apparatus according to claim 8, in which said control means further includes means for varying the operating temperature of said circuit.

* * * * *